(12) United States Patent
Huboux

(10) Patent No.: US 7,019,152 B2
(45) Date of Patent: Mar. 28, 2006

(54) PROCESS FOR THE OPTICAL RESOLUTION OF A PRECURSOR OF SCLAREOLIDE

(75) Inventor: Alexandre Huboux, Pringy (FR)

(73) Assignee: Firmenich SA, Geneva (CH)

( * ) Notice: Subject to any disclaimer, the term of this patent is extended or adjusted under 35 U.S.C. 154(b) by 146 days.

(21) Appl. No.: 10/820,709

(22) Filed: Apr. 9, 2004

(65) Prior Publication Data

US 2004/0192960 A1 Sep. 30, 2004

Related U.S. Application Data

(63) Continuation of application No. PCT/IB03/02933, filed on Jul. 24, 2003.

(30) Foreign Application Priority Data

Jul. 31, 2002 (WO) .................. PCT/IB02/03055

(51) Int. Cl.
*C07C 61/13* (2006.01)
*C07D 307/92* (2006.01)

(52) U.S. Cl. ............... 549/299; 549/204; 562/402; 562/466

(58) Field of Classification Search ........ 562/462, 562/497, 501, 402, 466; 549/204, 299
See application file for complete search history.

(56) References Cited

U.S. PATENT DOCUMENTS

| 5,247,100 A | * | 9/1993 | Gerke et al. | ................. 549/299 |
| 5,290,955 A | * | 3/1994 | Asanuma et al. | ........... 549/458 |
| 5,347,048 A | * | 9/1994 | Asanuma et al. | ........... 562/501 |
| 5,525,728 A | * | 6/1996 | Schneider et al. | .......... 549/299 |

FOREIGN PATENT DOCUMENTS

| EP | 0 550 889 A1 | 7/1993 |
| WO | WO 93/21174 | 10/1993 |

OTHER PUBLICATIONS

Article, XP-002256238, Ephedrin, PD 00-00, pp. 1181-1182 (1997).
T Sukasa Koga et al. XP004143697"Resolution of sclareolide as a key intermediate for the synthesis of AmbrokR" Tetrahedron, Asymmetry, Elsevier Science Publishers, Amsterdam, NL, vol. 9, No. 21, pp. 3819-3823 (1998).

* cited by examiner

*Primary Examiner*—Porfirio Nazario-Gonzalez
(74) *Attorney, Agent, or Firm*—Winston & Strawn LLP

(57) ABSTRACT

The present invention relates to the field of organic synthesis and more particularly to a new process for the optical resolution of a precursor of sclareolide. This process includes the reaction of [(1RS,2RS,4aSR,8aSR)-2-hydroxy-2,5,5,8a-tetramethyldecahydronaphthalen-1-yl]acetic acid, or an alkaline salt thereof, with an enantiomer of the 2-(methylamino)-1-phenyl-1-propanol, or an ammonium salt thereof respectively, which is used as resolving agent.

9 Claims, No Drawings

PROCESS FOR THE OPTICAL RESOLUTION OF A PRECURSOR OF SCLAREOLIDE

CROSS REFERENCE TO RELATED APPLICATIONS

This application is a continuation of International Application PCT/IB2003/002933 filed Jul. 24, 2003, the entire content of which is expressly incorporated herein by reference thereto.

TECHNICAL FIELD

The present invention relates to the field of organic synthesis and more particularly to a process for obtaining a compound of formula (I) or (I')

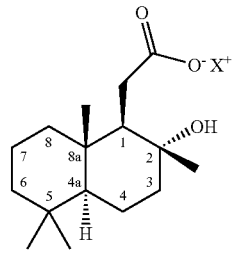

(I)

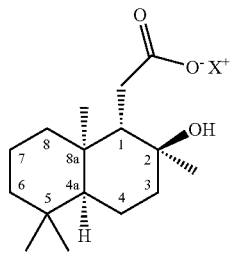

(I')

wherein X represents an optically active enantiomer of (2-hydroxy-1-methyl-2-phenylethyl)methylammonium;

using a racemic [(1RS,2RS,4aSR,8aSR)-2-hydroxy-2,5,5,8a-tetramethyldecahydronaphthalen-1-yl]acetic acid derivative as starting material. In other words, the invention's process concerns an optical resolution of a racemic [(1RS,2RS,4aSR,8aSR)-2-hydroxy-2,5,5,8a-tetramethyldecahydronaphthalen-1-yl]acetic acid derivative using, as resolving agent, an optically active enantiomer of 2-(methylamino)-1-phenyl-1-propanol.

BACKGROUND

[(1R,2R,4aS,8aS)-2-Hydroxy-2,5,5,8a-tetramethyldecahydronaphthalen-1-yl]acetic acid, from now on referred to also as (2R)-hydroxy-acid, may be a useful precursor of (+)-sclareolide, an intermediate in the synthesis of the perfumery ingredient (−)-Ambroxe®.

Despite this fact, only few processes for the preparation of (2R)-hydroxy-acid, or a salt thereof, by optical resolution of a racemic [(1RS,2RS,4aSR,8aSR)-2-hydroxy-2,5,5,8a-tetramethyldecahydronaphthalen-1-yl]acetic acid, from now on referred to also as (2RS)-hydroxy-acid, or a salt thereof, have been reported in the prior art.

In EP 550 889 is reported a process for the optical resolution of (2RS)-hydroxy-acid in which a 1-(aryl)ethylamine is used as resolving agent. For the same process, but using the sodium salt of (2RS)-hydroxy-acid as starting material, Koga et al. in Tetrahedron Asymmetry, (1998), 9, 3819, report the use as resolving agent of some 1,2- or 1,3-amino-alcohols in addition to the previously cited 1-(aryl)ethylamine.

However, all the prior art procedures suffer from the disadvantages of needing complex procedures implying slow and complicated crystallization procedures and/or a re-crystallization. Consequently, low yields of the final product are frequently, if not always, observed.

Therefore, there is a need for a process capable of providing an optically active enantiomer of a (2RS)-hydroxy-acid, or a salt thereof, and being of improved efficiency.

DETAILED DESCRIPTION OF THE PREFERRED EMBODIMENTS

In order to overcome the disadvantages of the prior art processes mentioned hereinabove, the present invention relates to a highly efficient process for obtaining a compound of formula (I) or (I')

(I)

(I')

wherein X represents an optically active enantiomer of (2-hydroxy-1-methyl-2-phenylethyl)methylammonium;
said process being characterized in that
a) it comprises the treatment of [(1RS,2RS,4aSR,8aSR)-2-hydroxy-2,5,5,8a-tetramethyldecahydronaphthalen-1-yl]acetic acid with an optically active enantiomer of 2-(methylamino)-1-phenyl-1-propanol, or the treatment of an alkaline salt of [(1RS,2RS,4aSR,8aSR)-2-hydroxy-2,5,5,8a-tetramethyldecahydronaphthalen-1-yl]acetic acid with an ammonium salt obtainable by the reaction of an optically active enantiomer of 2-(methylamino)-1-phenyl-1-propanol with an acid having a $pK_a$ below 5; and
b) said treatment is performed in a solvent wherein the compounds of formula (I) or (I') have different solubilities.

The expression "$pK_a$" has the usual meaning in the art, and in particular it represents—$\log_{10} K_a$, wherein $K_a$ is the dissociation constant of an acid in water, at standard temperature and pressure.

Compound (I) is a salt of [(1R,2R,4aS,8aS)-2-hydroxy-2,5,5,8a-tetramethyldecahydronaphthalen-1-yl]acetate, whereas compound (I') is a salt of [(1S,2S,4aR,8aR)-2-hydroxy-2,5,5,8a-tetramethyldecahydronaphthalen-1-yl]acetate.

Compounds (I) and (I') are also an object of the present invention. 2-(Methylamino)-1-phenyl-1-propanol, from now on, will be referred to also as pseudoephedrine.

Another object of the present invention concerns also the use of an optically active enantiomer of the pseudoephedrine, or an ammonium salt as defined above, for the optical resolution of (2RS)-hydroxy-acid, or an alkaline salt thereof respectively. In other words it concerns a method to obtain an optically active enantiomer of (2RS)-hydroxy-acid or an alkaline salt thereof, said method being characterized in that (2RS)-hydroxy-acid, or an alkaline salt thereof, is reacted with an optically active enantiomer of the pseudoephedrine, or an ammonium salt thereof as defined above respectively.

The racemic starting material, i.e. (2RS)-hydroxy-acid or an alkaline salt thereof, may be obtained by hydrolysis of (3aRS,5aSR,9aSR,9bRS)-3a,6,6,9a-tetramethyl-decahydronaphtho[2,1-b]furan-2(1H)-one, also known as (±)-sclareolide.

The hydrolysis may be performed according to any current method described in the prior art, e.g. as described by Koga et al. in Tetrahedron Asymmetry, (1998), 9, 3819 or by Goro et al. in EP 550 889. In general, the hydrolysis is performed by treating (±)-sclareolide with an alkaline base, such as NaOH, KOH or LiOH, in an alcoholic solvent, such as methanol or ethanol, to obtain the corresponding alkaline salt of (2RS)-hydroxy-acid. If desired, said alkaline salt may be transformed into (2RS)-hydroxy-acid by treating the former with an acid, preferably a strong inorganic acid such as HCl, HBr, $H_2SO_4$, $HNaSO_4$, $HKSO_4$, $HNO_3$, $H_3PO_4$, $HPF_6$, $HBF_4$, $HClO_4$, para-toluenesulphonic acid (TsOH), benzenesulphonic acid, methanesulphonic acid or the similar.

If the starting material used is an alkaline salt of (2RS)-hydroxy-acid, then said salt is preferably a $Na^+$, $K^+$ or $Li^+$ salt, and even more preferably a $Na^+$ salt.

As previously mentioned, as resolving agent is used an optically active enantiomer of pseudoephedrine, from now on referred to also as pseudoephedrine enantiomer. Said pseudoephedrine enantiomer can be used in the form of a free base or as an ammonium salt.

The pseudoephedrine enantiomer can be the (1S,2S) or the (1R,2R)-2-(methylamino)-1-phenyl-1-propanol. The enantiomeric purity, or enantiomeric excess (e.e.), of the pseudoephedrine enantiomer used will influence the efficiency of the invention process, the higher will be the e.e. of the pseudoephedrine enantiomer the more efficient will be the optical resolution of the (2RS)-hydroxy-acid or an alkaline salt thereof. Preferably the pseudoephedrine enantiomer will have an e.e. higher than 50%, or more preferably higher than 95%, or even higher than 98%.

If, in the optical resolution according to the invention, (2RS)-hydroxy-acid is used as starting material, then the pseudoephedrine enantiomer is used as a free base. Alternatively, if it is used an alkaline salt of (2RS)-hydroxy-acid, then the pseudoephedrine enantiomer is used in the form of an ammonium salt. The ammonium salt of the pseudoephedrine enantiomer may be employed in the invention's process as a preformed salt or may be generated in situ by reacting together the free base and an acid, for example in a quantity of about one equivalent of protons per free base. Suitable acids have a $pK_a$ below 5, and preferably comprised between 5 and −12. Non-limiting examples of such acids are selected from the group consisting of HX, wherein X is a halide, $H_2SO_4$, $HNO_3$, $H_3PO_4$, $HPF_6$, $HBF_4$, $HClO_4$, $C_1–C_{10}$ sulphonic acids, and $C_1–C_{10}$ mono-, di- or tri-carboxylic acid. In particular one may cite the following HCl, HBr, $HClO_4$, $H_2SO_4$, $HNaSO_4$, $HKSO_4$, $HNO_3$, $H_3PO_4$, $HPF_6$, $HBF_4$, para-toluenesulphonic acid (TsOH), benzenesulphonic acid, methanesulphonic acid, oxalic acid, citric acid, acetic acid or propionic acid.

Thus, non-limiting examples of the anion of the ammonium salt can be $Cl^-$, $Br^-$, $ClO_4^-$, $SO_4^{2-}$, $HSO_4^-$, $NO_3^-$, $H_2PO_4^-$, $HPO_4^{2-}$, $PF_6^-$, $BF_4^-$, $ClO_4^-$, para-toluenesulphonate, benzenesulphonate, methanesulphonate, acetate or propionate.

The pseudoephedrine enantiomer, in any of the above-mentioned forms, may be added in amounts comprised between 0.35 and 1.2 molar equivalent with respect to the (2RS)-hydroxy-acid or of the alkaline salt of (2RS)-hydroxy-acid, preferably between 0.5 and 1.0 equivalents, even more preferably between 0.6 and 0.8 equivalents.

The principle of the present optical resolution is based on the solubility difference of the diastereomeric salts of formula (I) or (I'). It is therefore possible to precipitate preferentially only one of the compounds of formula (I) or (I').

It has been found that, in general, when the (1R,2R)-pseudoephedrine is used then the precipitate comprises a majority of compound of formula (I) (wherein X represents ((1R,2R)-2-hydroxy-1-methyl-2-phenylethyl)methylammonium), and the liquor comprises a majority of compound of formula (I'). Vice versa when the (1S,2S)-pseudoephedrine is used, the liquor comprises a majority of compound of formula (I), and the precipitate comprise a majority of compound of formula (I').

By "a majority of compound" we mean here at least 60%, preferably at least 75%, of compound of formula (I) or (I'); or even at least 95%.

The optical resolution of the invention's process is carried out in a solvent wherein the compound of formula (I) and the compound of formula (I') have different solubilities. Examples of such solvents are $C_6–C_9$ aromatic solvents, such as toluene, xylene or benzene, $C_6–C_{10}$ petroleum fractions or hydrocarbons, such as cyclohexane or heptane, $C_1–C_2$ halogenated solvents, such as chloroform or dichloromethane, $C_4–C_{10}$ ethers, such as tetrahydrofurane, anisole, ter-amyl methyl ether or ter-butyl methyl ether, $C_3–C_{10}$ esters, such as ethyl acetate, ethyl propionate or isopropyl acetate, $C_3–C_{10}$ alcohols, such as isopropanol or cyclohexylmethanol, or mixtures thereof. Said solvents may be anhydrous or contain water up to 50% of its own weight. By "anhydrous solvent" it is meant here a solvent which contains less than 1% of its own weight of water, or even less than 0.5%.

Preferably, the solvent is selected from the group consisting of anhydrous tetrahydrofuran, toluene, xylene, benzene or cyclohexane.

As mentioned above, the compounds of formula (I) or (I') obtained according to the invention's process are useful intermediates, or starting material, for the preparation of (+)-sclareolide ((3aR,5aS,9aS,9bR)-3a,6,6,9a-tetramethyl-decahydronaphtho[2,1-b]furan-2(1H)-one) or (−)-sclareolide ((3aS,5aR,9aR,9bS)-3a,6,6,9a-tetramethyldecahydro-naphtho[2,1-b]furan-2(1H)-one), respectively.

Therefore, another aspect of the invention concerns the use of a compound of formula (I) or (I') for the synthesis of (+)-sclareolide or (−)-sclareolide, respectively, and in particular, a process for obtaining (+)-sclareolide or (−)-sclareolide, said process being characterized in that it comprises i) the treatment of a compound of formula (I), or (I') respectively, with an acid having a $pK_a$ below 5, followed by ii) a thermal treatment at a temperature comprised between 60° C. and 150° C.

This process allows the conversion of compound (I) into (+)-sclareolide, or compound (I') into (−)-sclareolide. This process may be performed according to any standard method for the generation of a lactone from a hydroxy-acid or salt thereof.

For example, the conversion of compound (I) into the (+)-sclareolide can be performed by treating, for example at room temperature, compound of formula (I) with a strong mineral acid, such as defined above, to recover (2R)-hydroxy-acid. N on-limiting examples of such acids are HCl, HBr, $HClO_4$, $H_2SO_4$, $HNaSO_4$, $HKSO_4$, $HNO_3$, $H_3PO_4$, $HPF_6$, $HBF_4$, $C_1$–$C_{10}$ sulphonates, such as para-toluenesulphonic acid (TsOH), benzenesulphonic acid, methanesulphonic acid, or the similar.

Subsequently, (2R)-hydroxy-acid is treated with a catalytic quantity of an acid such as acetic or propionic acid, but a strong acid may also be used. The strong mineral acid is used in amounts comprised between 0.95 and 1.05 equivalent of proton in respect to the compound of formula (I), and the catalytic acid preferably in amounts comprised between 0.01 and 0.15, preferably between 0.03 and 0.10, equivalent of proton in respect of the compound of formula (I), but higher amounts of catalytic acids can also be used.

This reaction step is carried out in the presence of a solvent. Non-limiting examples of such a solvent include $C_6$–$C_9$ aromatic solvents such as benzene, toluene or xylene, $C_6$–$C_{10}$ hydrocarbon solvents such as cyclohexane, $C_4$–$C_{10}$ ethers or mixtures thereof. However aromatic solvents are preferred. During the formation of the (+)-sclareolide it may be useful to remove the water which is formed, e.g. by azeotropic distillation.

The temperature at which the conversion of the (2R)-hydroxy-acid into (+)-sclareolide may be carried out is comprised between 60° C. and 150° C., preferably between 95° C. and 125° C.

Alternatively the conversion into (+)-sclareolide can be achieved by reacting directly the compound of formula (I) with an excess of a strong acid, for example in an amount comprised between 1.01 and 1.15 equivalent of proton in respect of the latter, and at a temperature comprised between 60° C. and 150° C.

It is understood that, if desired, the same processes described above can be applied to obtain (−)-sclareolide.

Considering that the starting racemic (2RS)-hydroxy-acid or a salt thereof may be obtained from the racemic (±)-sclareolide, a process comprising the following reaction steps:

I) the hydrolysis, as described above, of (±)-sclareolide into the corresponding (2RS)-hydroxy-acid or an alkaline salt thereof, by means of an alkaline base;

II) a process as defined above to isolate a compound of formula (I) or (I'); and III) the conversion of the compound of formula (I), or (I'), into (+)-sclareolide, or (−)-sclareolide respectively, by a process as defined above;

allows to isolate (+)-sclareolide, or (−)-sclareolide, from the racemic (±)-sclareolide in high yields, high e.e. and, in general, without any re-crystallization or complex procedure, to the contrary of what is described in the prior art. Such a process is a further object of the invention.

Typical yields of such a process, which is also an object of the invention, are in the range of 80%, based on the amount of (+)-sclareolide, or (−)-sclareolide, present in the starting racemic sclareolide, or even, e.g., more than 90%. Typical e.e. of (+)-sclareolide, or (−)-sclareolide, obtained at the end of this particular embodiment of the invention are higher than 50%, but preferably higher than 90% or even 95%. Such results are quite unexpected in view of the above-cited prior art.

EXAMPLES

The invention will now be described in further detail by way of the following examples, wherein the abbreviations have the usual meaning in the art, the temperatures are indicated in degrees centigrade (° C.); $^1$H-NMR spectral data were recorded at 400 MHz and $^{13}$C NMR spectra were recorded at 100 MHz in DMSO, the chemical displacements δ are indicated in ppm with respect to the TMS as standard, the coupling constants J are expressed in Hz and all the abbreviations have the usual meaning in the art.

EXAMPLE 1

Isolation of (1R,2R)-1-hydroxy-N-methyl-1-phenyl-2-propanaminium [(1R,2R,4aS,8aS)-2-hydroxy-2,5,5,8a-tetramethyldecahydronaphthalen-1-yl]acetate (a Compound of Formula (I))

In a 2 liter, three-necked, round-bottomed flask equipped with a reflux condenser, a mechanical stirrer and containing 1.01 of dry tetrahydrofuran (THF) were introduced 268.4 g (1.00 mole) of (2RS)-hydroxy-acid (obtained according to EP 550889) and 119.8 g (0.725 mole) of (1R, 2R)-pseudoephedrine. The resulting suspension was heated to reflux for 1 hour and the temperature was then gradually lowered to room temperature over 2 h 30 min. The suspension was filtered and the precipitate washed twice with 250 ml of dry THF. The resulting solid was dried under vacuum to give 199.1 g (0.459 mole, yield=92%) of the title salt.

$^1$H-NMR:7.35–7.23 (m, 5H, Ph-H); 4.28 (d, 1H, J=7.6 Hz, CH(OH)); 2.69 (dq, J=7.6 and 6.6 Hz, 1H, CH(NH$_2$(CH$_3$))); 2.36 (s, 3H, NH$_2$CH$_3$); 2.33 (dd, J=16, 4.2 Hz, 1H, CHCOO); 2.02 (dd, J=16, 6.3 Hz, 1 H, CHCOO); 1.75 (dd, J=6.3 4.2 Hz, 1H, CH(CH$_2$)COO); 1.72–1.03 (m, 10H, 5CH$_2$); 0.96 (s, 3H, CH$_3$CH(OH)); 0.91 (m, 1H, CHC(CH$_3$)$_2$); 0.84 (s, 3H, C(CH$_3$)$_2$); 0.76 (s, 3H, C(CH$_3$)$_2$); 0.75 (d, J=6.6 Hz, 3H, CH$_3$CHNH$_2$(CH$_3$)); 0.73 (s, 3H, CCH$_3$).

$^{13}$C-NMR: 176.6 (s); 143.1 (s); 127.8 (d); 127.1 (d); 127.0 (d); 75.6 (d); 70.9 (s); 60.2 (d); 56.3 (d); 55.5 (d); 43.7 (t); 41.4 (t); 38.57 (s); 37.9 (t); 33.2 (q); 32.8 (s); 32.5 (q); 30.5 (t); 24.0 (q); 21.3 (q); 19.9 (t); 17.9 (t); 14.9 (q); 14.4 (q).

EXAMPLE 2

Conversion of (1R,2R)-1-hydroxv-N-methyl-1-phenyl-2-propanaminium [(1R,2R,4aS,8aS)-2-hydroxy-2,5,5,8a-tetramethyldecahydronalphthalen-1-yl]acetate into (+)-sclareolide To a suspension of 199.1 g of the compound of formula (I), obtained-according to example 1, in 550 g of toluene were added dropwise, at T=20–5° C. and over 30 minutes, 230 g of 10% aqueous sulphuric acid. The reaction mixture was heated to 50° C. and, after the removal of the aqueous phase, the organic layer was washed twice with 50 ml of water. To the toluene phase, containing the free (2R)- hydroxy-acid, were added 6.9 g of acetic acid and the reaction mixture was heated at reflux for 2.75 hours, using a Dean-Stark trap to remove water azeotropically. At the end of the reflux period, the reaction mixture was cooled to approximately 50° C., washed with 100 ml of water and then with 100 ml of 3% aqueous NaHCO$_3$. It was thus obtained an organic phase which, after evaporation of the solvent, provided 113.6 g (91% yield) of (+)-sclareolide having a purity >98% and an e.e.=99%, purity and e.e. being obtained by chiral GC. The NMR spectra of the product thus obtained were conform to those reported in the prior art.

What is claimed is:

1. A compound of formula (I) or (I')

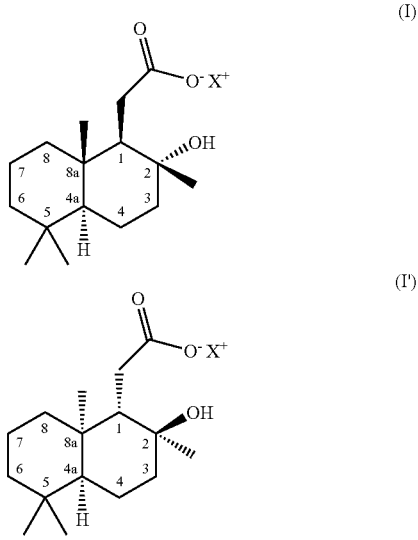

wherein X represents an optically active enantiomer of (2-hydroxy-1-methyl-2-phenylethyl)methylammonium.

2. A process for obtaining a compound of formula (I) or (I'), as defined in claim 1, said process being characterized in that
a) it comprises the treatment of [(1RS,2RS,4aSR,8aSR)-2-hydroxy-2,5,5,8a-tetramethyldecahydronaphthalen-1-yl]acetic acid with an optically active enantiomer of 2-(methylamino)-1-phenyl-1-propanol, or the treatment of an alkaline salt of [(1RS,2RS,4aSR,8aSR)-2-hydroxy-2,5,5,8a-tetramethyldecahydronaphthalen-1-yl]acetic acid with an ammonium salt obtainable by the reaction of an optically active enantiomer of 2-(methylamino)-1-phenyl-1-propanol with an acid having a pK$_a$ below 5; and
b) said treatment is performed in a solvent wherein the compounds of formula (I) or (I') have different solubilities.

3. A process according to claim 2, wherein the solvent is a $C_6$–$C_9$ aromatic solvent, a $C_6$–$C_{10}$ petroleum fraction or hydrocarbon, a $C_1$–$C_2$ halogenated solvent, a $C_4$–$C_{10}$ ether, a $C_3$–$C_{10}$ ester, a $C_3$–$C_{10}$ alcohol or mixtures thereof.

4. A process according to claim 3, wherein the solvent is selected from the group consisting of anhydrous tetrahydrofuran, toluene, xylene, benzene or cyclohexane.

5. A process according to claim 2, wherein the optically active enantiomer of 2-(methylamino)-1-phenyl-1-propanol is (1R,2R)-2-(methylamino)-1-phenyl-1-propanol or (1S,2S)-2-(methylamino)-1-phenyl-1-propanol.

6. A process according to claim 2, wherein the acid having a pK$_a$ below 5 is selected from the group consisting of HX, wherein X is a halide, H$_2$SO$_4$, HNO$_3$, H$_3$PO$_4$, HPF$_6$, HBF$_4$, HClO$_4$, $C_1$–$C_{10}$ sulphonic acids, and $C_1$–$C_{10}$ mono-, di- or tri-carboxylic acid.

7. A process for obtaining (+)-sclareolide or (−)-sclareolide which comprises treating a compound of formula (I) or (I'), respectively, as defined as in claim 1, with an acid having a pK$_a$ below 5 and by a thermal treatment at a temperature comprised between 60° C. and 150° C.

8. A process for obtaining (+)-sclareolide or (−)-sclareolide said process being characterized in that it comprises
I) the hydrolysis of (±)-sclareolide into a corresponding [(1RS,2RS,4aSR,8aSR)-2-hydroxy-2,5,5,8a-tetramethyldecahydronaphthalen-1-yl]acetic acid or a salt thereof,
II) treatment of [(1RS,2RS,4aSR,8aSR)-2-hydroxy-2,5,5,8a-tetramethyldecahydro naphthalen-1-yl]acetic acid with an optically active enantiomer of 2-(methylamino)-1-phenyl- 1-propanol, or the treatment of an alkaline salt of [(1RS,2RS,4aSR,8aSR)-2-hydroxy-2,5,5,8a-tetramethyldecahydronaphthalen-1-yl]acetic acid with an ammonium salt obtainable by the reaction of an optically active enantiomer of 2-(methylamino)-1-phenyl-1-propanol with an acid having a pK$_a$ below 5; wherein either treatment is performed in a solvent to obtain a compound of formula (I) or (I'), respectively, according to claim 1; and
III) treating the compound of formula (I) or (I'), respectively, with an acid having a PK$_a$ below 5 and by a thermal treatment at a temperature comprised between 60° C. and 150° C.

9. A process for obtaining a compound of formula (I) or (I'), as defined in claim 1, said process being characterized in that
a) it comprises the treatment of [(1RS,2RS,4aSR,8aSR)-2-hydroxy-2,5,5,8a-tetramethyldecahydronaphthalen-1-yl]acetic acid with an optically active enantiomer of 2-(methylamino)-1-phenyl-1-propanol, or the treatment of an alkaline salt of [(1RS,2RS,4aSR,8aSR)-2-hydroxy-2,5,5,8a-tetramethyldecahydronaphthalen-1-yl]acetic acid with an ammonium salt obtainable by the reaction of an optically active enantiomer of 2-(methylamino)-1-phenyl-1-propanol with an acid selected from the group consisting of HX, wherein X is a halide, H$_2$SO$_4$, HNO$_3$, H$_3$PO$_4$, HPF$_6$, HBF$_4$, HClO$_4$, $C_1$–$C_{10}$ sulphonic acids, and $C_1$–$C_{10}$ mono-, di- or tri-carboxylic acid.; and
b) said treatment is performed in a solvent selected from the group consisting of a $C_6$–$C_9$ aromatic solvent, a $C_6$–$C_{10}$ petroleum fraction or hydrocarbon, a $C_1$–$C_2$ halogenated solvent, a $C_4$–$C_{10}$ ether, a $C_3$–$C_{10}$ ester, a $C_3$–$C_{10}$ alcohol or mixtures thereof.

* * * * *

UNITED STATES PATENT AND TRADEMARK OFFICE
CERTIFICATE OF CORRECTION

PATENT NO. : 7,019,152 B2  Page 1 of 2
APPLICATION NO. : 10/820709
DATED : March 28, 2006
INVENTOR(S) : Huboux It is certified that error appears in the above-identified patent and that said Letters Patent is hereby corrected as shown below:

Title Page,
Item [56] References Cited, OTHER PUBLICATIONS,
"T Sukasa Koga et al." reference, change "T Sukasa to --Tsukasa --; and change "AmbrokR" to -- Ambrox® --.

Column 1,
Lines 29-39, delete formula (I') and insert the following:

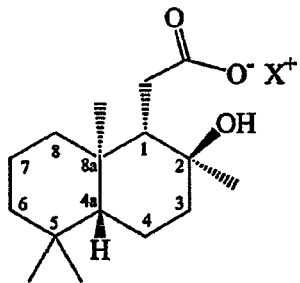

Column 7,
Lines 26-36, delete formula (I') and insert the following:

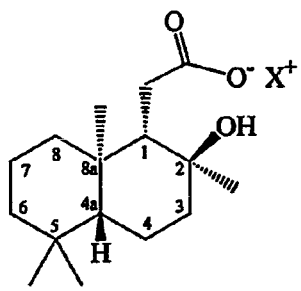

UNITED STATES PATENT AND TRADEMARK OFFICE
CERTIFICATE OF CORRECTION

PATENT NO. : 7,019,152 B2
APPLICATION NO. : 10/820709
DATED : March 28, 2006
INVENTOR(S) : Huboux It is certified that error appears in the above-identified patent and that said Letters Patent is hereby corrected as shown below:

Column 7,
Lines 36-46, delete formula (I') and insert the following:

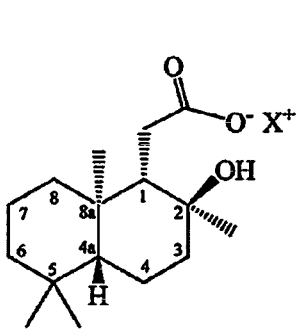

(I')

Line 52, (claim 2, line 13), delete " $pK_a$ " and insert -- $pK_a$ --.

Signed and Sealed this

Seventh Day of November, 2006

JON W. DUDAS
*Director of the United States Patent and Trademark Office*